US008541614B2

(12) United States Patent
Broggini et al.

(10) Patent No.: US 8,541,614 B2
(45) Date of Patent: Sep. 24, 2013

(54) PROCESS FOR THE PREPARATION OF (−)-(4-CHLORO-PHENYL)-(3-TRIFLUOROMETHYL-PHENOXY)-ACETIC ACID 2-ACETYLAMINO-ETHYL ESTER

(75) Inventors: Diego Broggini, Armin-Bollinger-weg (CH); Hartmut Burghard Zinser, J. J. Wepferstrasse (CH)

(73) Assignee: Metabolex, Inc., Hayward, CA (US)

( * ) Notice: Subject to any disclaimer, the term of this patent is extended or adjusted under 35 U.S.C. 154(b) by 110 days.

(21) Appl. No.: 12/417,671

(22) Filed: Apr. 3, 2009

(65) Prior Publication Data

US 2010/0093854 A1 Apr. 15, 2010

Related U.S. Application Data

(60) Provisional application No. 61/042,078, filed on Apr. 3, 2008.

(51) Int. Cl.
*C07C 69/76* (2006.01)

(52) U.S. Cl.
USPC ............................................ 560/62; 514/559

(58) Field of Classification Search
None
See application file for complete search history.

(56) References Cited

U.S. PATENT DOCUMENTS

| 3,517,050 | A | | 6/1970 | Bolhofer | |
|---|---|---|---|---|---|
| 3,953,490 | A | | 4/1976 | Shuman | |
| 6,262,118 | B1 | * | 7/2001 | Luskey et al. | 514/559 |
| 7,714,131 | B2 | * | 5/2010 | Zhu et al. | 544/387 |

FOREIGN PATENT DOCUMENTS

| JP | 2009019004 A | 1/2009 |
|---|---|---|
| WO | WO 2007/038243 A | 4/2007 |

OTHER PUBLICATIONS

Mar., Advanced Organic Chemistry, 6$^{th}$ Edition, 2007, pp. 1402-1403.*
Barrett-Conner, E.,"Epidemiology, Obesity, and Non-Insulin-Dependent Diabetes Mellitus.", Epidemiologic Reviews, 1989, vol. 11, pp. 172-181.
Bell et al., "Glucokinase Mutations, Insulin Secretion, and Diabetes Mellitus.", Annu. Rev. Physiol., 1996, vol. 58, pp. 171-186.
Fajans et al., "Maturity Onset Diabetes of the Young (MODY).", Diabetic Medicine, 1996, vol. 13, pp. S90-S95.
Flier, J., "Insulin Receptors and Insulin Resistance.", Ann Rev. Med., 1983, vol. 34, pp. 145-160.
Garcia et al., "Morbidity and Morality in Diabetics in the Framingham Population.", Diabetes, 1974, vol. 23, pp. 105-111.
Howard et al., "Lipoprotein Composition in Diabetes Mellitus.", Atherosclerosis, 1978, vol. 30, pp. 153-162.
Jain et al., "Erythrocyte Membrane Lipid Peroxidation and Glysosylated hemoglobin in Diabetes.", Diabetes, 1989, vol. 38, pp. 1539-1543.
Joslin, E.P., "Arteriosclerosis and Diabetes.", Annals of Clinical Medicine, 1927, vol. 5 (12), pp. 1061-1079.
Kaplan et al., "Cardiovascular diseases.", *Health and Human Behavior* 1993, Chapter 10, pp. 206-242, McGraw-Hill, New York.
Knowler et al., "Obesity in the Pima Indians: its magnitude and relationship with diabetes.", Am. J Clin. Nutr., 1991, vol. 53, pp. 1543-1551, USA.
Laakso, M. and Lento, S., " Epidemiology of macrovascular disease in diabetes.", Diabetes Reviews, 1997, vol. 5(4), pp. 294-315.
Peters et al., "A Clinical Approach for the Diagnosis of Diabetes Mellitus.", JAMA, 1996, vol. 276(15), pp. 1246-1252.
Reaven, G. M., "Insulin Resistance and Human Disease a Short History.", Basic & Clin. Phys. & Pharm., 1998, vol. 9, pp. 387-406.
Reaven, G.M., "Pathophysiology of Insulin Resistance in Human Disease.", Physiological Reviews, 1995, vol. 75, pp. 473-486.
The Expert Committee on the Diagnosis and Classification of Diabetes Mellitus, Diabetes Care, 1999, vol. 2 (Suppl 1), pp. S5-S19.
Beyer, Walter "Lehrbuch der organischem Chemie", 1984, S. Hirzel Verlag, Stuttgart, p. 245, lines 1, 2, XP002529114.
Database CA, Fujii et al., "Preparation of optically active aryloxycarboxylic acids.", XP002529115, Database accession No. 2009:111897 abstract, JP 2009019004 A; Jan. 29, 2009, paragraphs [0026], [0081], [0091].
International Search Report-International Application No. PCT/EP2009/053971, Date of Mailing of International Search Report, Aug. 28, 2009. Republished on Oct. 8, 2009.
Written Opinion relating to International Application No. PCT/EP2009/053971, Date of Mailing of Written Opinion, Aug. 28, 2009.

* cited by examiner

*Primary Examiner* — Sudhakar Katakam
(74) *Attorney, Agent, or Firm* — Hamilton DeSanctis & Cha, LLP

(57) ABSTRACT

The present invention is directed to a novel process for the preparation of (4-chloro-phenyl)-(3-trifluoromethyl-phenoxy)-acetic acid 2-acetylamino-ethyl ester, useful in the treatment of metabolic disorders and further to a process for the preparation of (4-chloro-phenyl)-(3-trifluoromethyl-phenoxy)-acetic acid, a synthesis intermediate.

27 Claims, No Drawings

PROCESS FOR THE PREPARATION OF (−)-(4-CHLORO-PHENYL)-(3-TRIFLUOROMETHYL-PHENOXY)-ACETIC ACID 2-ACETYLAMINO-ETHYL ESTER

CROSS REFERENCE TO RELATED APPLICATION

This application claims the benefit of U.S. Provisional Application No. 61/042,078, filed Apr. 3, 2008, which is incorporated by reference herein.

FIELD OF THE INVENTION

The present invention is directed to a novel process for the preparation of (−)-(4-chloro-phenyl)-(3-trifluoromethyl-phenoxy)-acetic acid 2-acetylamino-ethyl ester, useful in the treatment of metabolic disorders and further to a process for the preparation of (−)-(4-chloro-phenyl)-(3-trifluoromethyl-phenoxy)-acetic acid, a synthesis intermediate.

BACKGROUND OF THE INVENTION

Diabetes mellitus, commonly called diabetes, refers to a disease process derived from multiple causative factors and characterized by elevated levels of plasma glucose, referred to as hyperglycemia. (See, e.g. LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as noninsulin dependent diabetes or NIDDM). Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies. Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998; this reference and all references cited therein are herein incorated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105-11 (1974); and Laakso, M. and Lehto, S., Diabetes Reviews (1997) 5(4): 294-315). Several lipoprotein abnormalities have been described among diabetic subjects (Howard B., et al., Artherosclerosis (1978) 30: 153-162).

Luskey, K. L., et al., in U.S. Pat. No. 6,262,118, issued Jul. 17, 2001 disclose the use of (−)-(3-trifalomethylphenoxy)-(4-halophenyl)-acetic acid derivatives for the treatment of insulin resistance, Type 2 diabetes and hyperlipidemia.

SUMMARY OF THE INVENTION

The present invention is directed to a process for the preparation of compounds of formula (I)

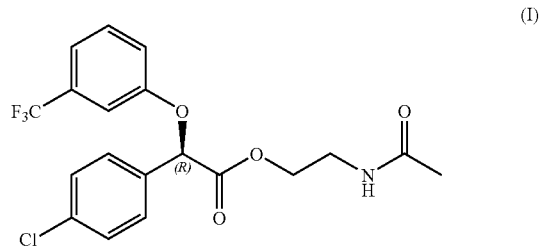

also known as (−)-(4-chloro-phenyl)-(3-trifluoromethyl-phenoxy)-acetic acid 2-acetylamino-ethyl ester, comprising

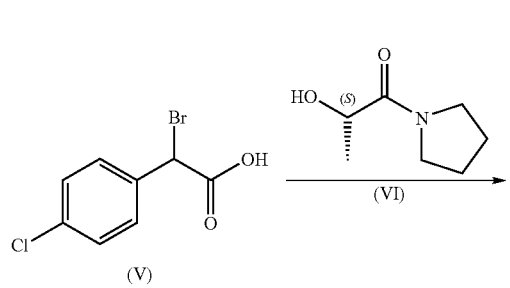

(V)

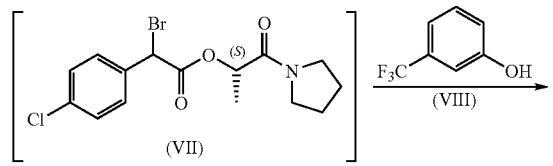

(VII)

reacting compound of formula (V), with a compound of formula (VI); in the presence of a first catalyst; in the presence of coupling agent; in an aprotic organic solvent or mixture thereof; to yield the corresponding compound of formula (VII);

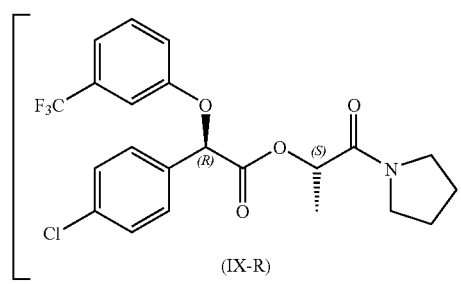

reacting the compound of formula (VII) with a compound of formula (VIII) wherein the compound of formula (VIII) is present as its corresponding salt; in the presence of a second catalyst; in an organic solvent or mixture thereof; to yield the corresponding compound of formula (IX-R);

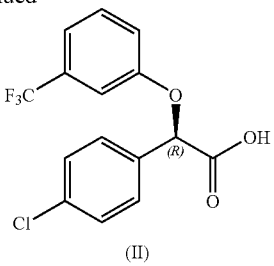

(II)

reacting the compound of formula (IX-R) with an acid; to yield the corresponding compound of formula (II);

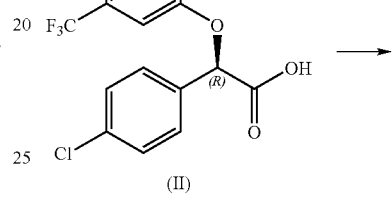

(X)

reacting the compound of formula (II) with a source of chlorine; neat or in an organic solvent; to yield the corresponding compound of formula (X);

reacting the compound of formula (X) with a compound of formula (XI); neat or in an organic solvent; to yield the corresponding compound of formula (I).

In an embodiment, the present invention is directed to a process for the preparation of a compound of formula (I)

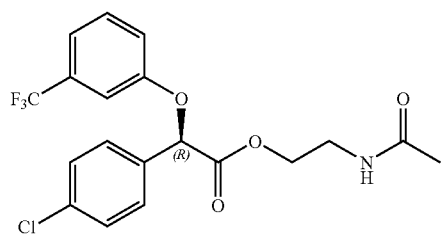

also known as (−)-(4-chloro-phenyl)-(3-trifluoromethyl-phenoxy)-acetic acid 2-acetylamino-ethyl ester, comprising

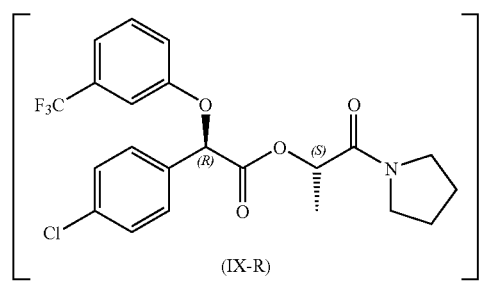

reacting the compound of formula (IX-R) with an acid; to yield the corresponding compound of formula (II);

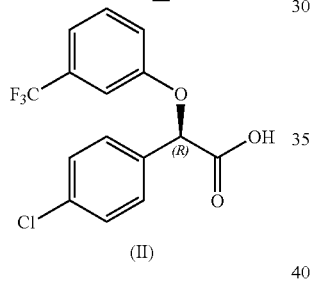

reacting the compound of formula (II) with a source of chlorine; neat or in an organic solvent; to yield the corresponding compound of formula (X);

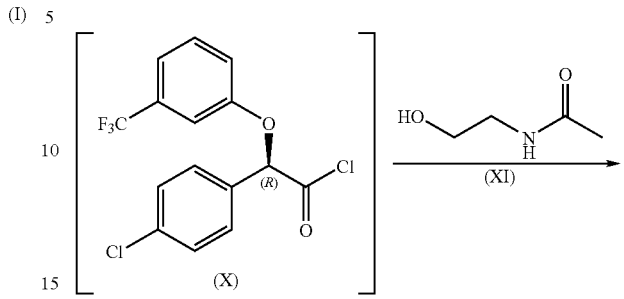

reacting the compound of formula (X) with a compound of formula (XI); neat or in an organic solvent; to yield the corresponding compound of formula (I).

The present invention is further directed to a process for the preparation of a compound of formula (II)

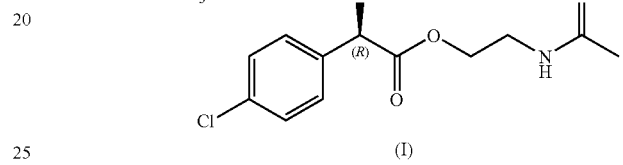

comprising

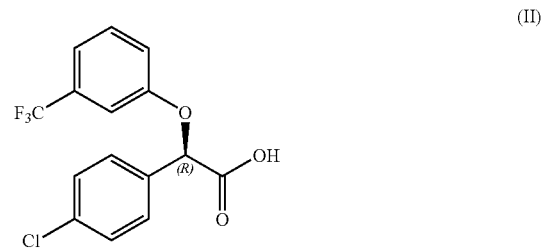 [SMILES: O=C(O)[C@H](Oc1cccc(C(F)(F)F)c1)c1ccc(Cl)cc1]

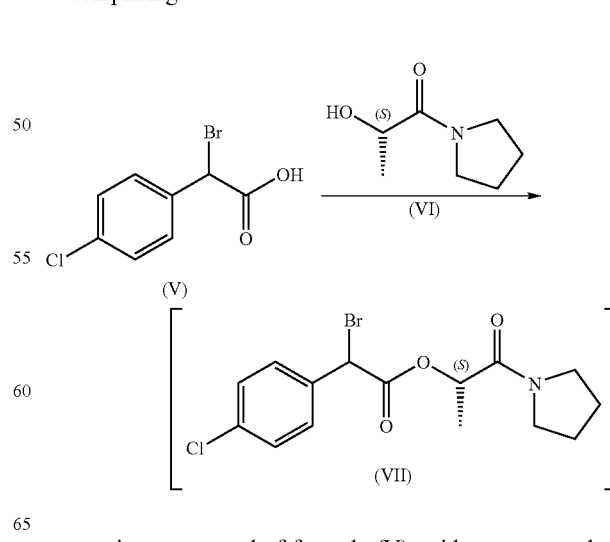

reacting compound of formula (V), with a compound of formula (VI); in the presence of a first catalyst; in the presence of coupling agent; in an aprotic organic solvent or mixture thereof; to yield the corresponding compound of formula (VII);

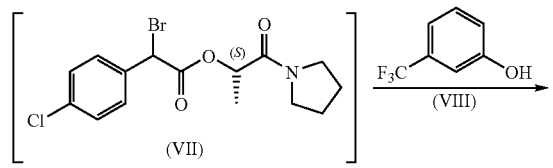

reacting the compound of formula (VII) with a compound of formula (VIII) wherein the compound of formula (VIII) is present as its corresponding salt; in the presence of a second catalyst; in an organic solvent or mixture thereof; to yield the corresponding compound of formula (IX-R);

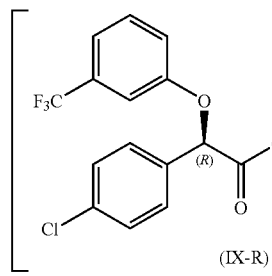

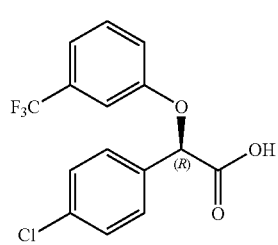

reacting a compound of formula (IX-R) with an acid; to yield the corresponding compound of formula (II).

In an embodiment, the present invention is directed to a process for the preparation of a compound of formula (II) comprising

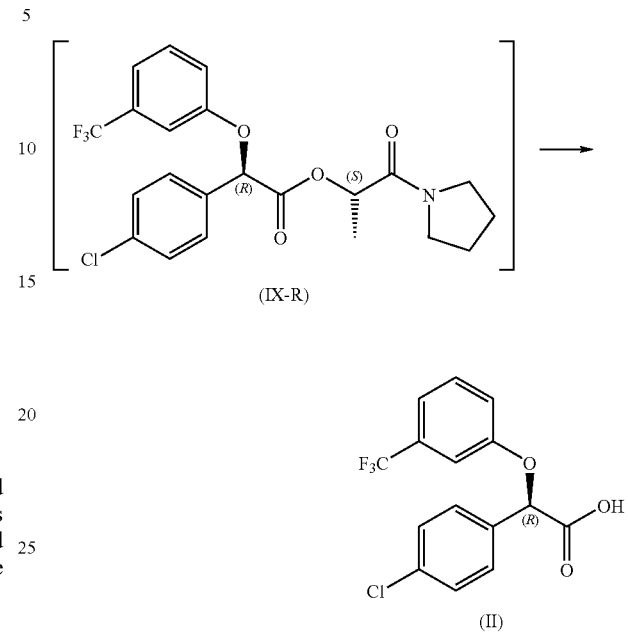

reacting a compound of formula (IX-R) with an acid; to yield the corresponding compound of formula (II).

The present invention is further directed to a process for the recrystallization of the compound of formula (I), as described in more detail herein. The present invention is further directed to a product prepared according to any of the processes described herein.

Illustrative of the invention is a pharmaceutical composition comprising a pharmaceutically acceptable carrier and a product prepared according to any of processes described herein. An illustration of the invention is a pharmaceutical composition made by mixing a product prepared according to any of processes described herein and a pharmaceutically acceptable carrier. Illustrating the invention is a process for making a pharmaceutical composition comprising mixing a product prepared according to any of processes described herein and a pharmaceutically acceptable carrier.

Exemplifying the invention are methods of treating a metabolic disorder (preferably a metabolic disorder selected from the group consisting of impaired oral glucose tolerance, elevated blood glucose levels, insulin resistance, hyperglycemia, hyperinsulinemia, elevated $HBA_{1c}$ levels, elevated triglycerides, diabetes, dyslipidemia and hyperlipidemia) in a subject in need thereof comprising administering to the subject a therapeutically effective amount of a product prepared according to any of processes described herein or any of the pharmaceutical compositions described above.

Another example of the invention is the use of a product prepared according to any of processes described herein in the preparation of a medicament for treating: (a) impaired oral glucose tolerance, (b) elevated blood glucose levels, (c) insulin resistance, (d) hyperglycemia, (e) hyperinsulinemia, (f) elevated $HBA_{1c}$ levels, (g) elevated triglycerides, (h) diabetes, (i) dyslipidemia or (j) hyperlipidemia, in a subject in need thereof.

DETAILED DESCRIPTION OF THE INVENTION

The present invention is directed to a process for the preparation of a compound of formula (I)

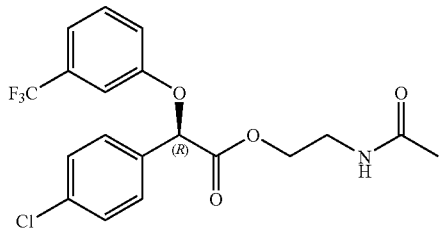

useful in the treatment of metabolic disorders. The present invention is further directed to a process for the recrystallization of the compound of formula (I), as described in more details herein. Compounds of formula (I) prepared according to the processes described herein are useful for the treatment of metabolic disorders, including but not limited to impaired oral glucose tolerance, elevated blood glucose levels, insulin resistance, hyperglycemia, hyperinsulinemia, elevated $HBA_{1c}$ levels, elevated triglycerides, diabetes, dyslipidemia and hyperlipidemia; preferably insulin resistance, diabetes (more preferably Type 2 diabetes) and hyperlipidemia. The present invention is further directed to a process for the preparation of a compound of formula (II)

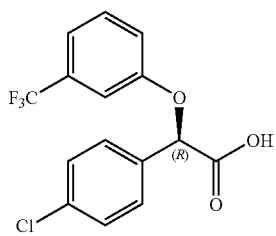 [SMILES: O=C(O)[C@H](Oc1cccc(C(F)(F)F)c1)c1ccc(Cl)cc1]

useful as an intermediate in the synthesis of the compound of formula (I).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isolated form" shall mean that the compound is present in a form which is separate from any solid mixture with another compound(s), solvent system or biological environment. In an embodiment of the present invention, the compound of formula (I) is prepared in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is prepared in a substantially pure form. In another embodiment, the present invention is directed to a process for the preparation of a compound of formula (I) in a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is prepared in a form which is substantially free of corresponding salt form(s). In another embodiment, the present invention is directed to a process for the preparation of a compound of formula (I), wherein the compound of formula (I) is substantially free of corresponding salt form(s).

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "modulate" refers to the treating, prevention, suppression, enhancement or induction of a function or condition. For example, the compounds prepared according to the processes described herein can modulate hyperlipidemia by lowering cholesterol in a human, thereby suppressing hyperlipidemia.

As used herein, the term "treating" means the management and care of a human subject for the purpose of combating the disease, condition, or disorder and includes the administration of a compound of the present invention to prevent the onset of the symptoms or complications, alleviating the symptoms or complications, or eliminating the disease, condition, or disorder.

As used herein, the term "composition" is intended to encompass a product comprising the specified ingredients in the specified amounts, as well as any product which results, directly or indirectly, from combinations of the specified ingredients in the specified amounts.

As used herein, the term "metabolic disorders" include disorders associated with the metabolic system. Suitable examples include, but are not limited to impaired oral glucose tolerance, elevated blood glucose levels, insulin resistance, hyperglycemia, hyperinsulinemia, elevated $HBA_{1c}$ levels, elevated triglycerides, diabetes, dyslipidemia and hyperlipidemia.

As used herein, the term "insulin resistance" shall mean a disorder of glucose metabolism. More specifically, insulin resistance can be defined as the diminished ability of insulin to exert its biological action across a broad range of concentrations producing less than the expected biologic effect. (see, e.g., Reaven, G. M., *J. Basic & Clin. Phys. & Pharm.* (1998) 9: 387-406 and Flier, J. *Ann Rev. Med.* (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1), has been referred to as "Syndrome X" (see, e.g., Reaven, G. M., *Physiol. Rev.* (1995) 75: 473-486).

As used herein, the terms "diabetes mellitus" or "diabetes" mean a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described herein, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes. The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* (1996) (9 Suppl 6): S90-5 and Bell, G. et al., *Annu. Rev. Physiol.* (1996) 58: 171-86; genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenyloin) or inhibit insulin action (e.g., estrogens and glucocorticoids); and diabetes caused by infection (e.g., rubella, Coxsackie, and CMV); as well as other genetic syndromes. The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol 2 (Suppl 1): S5-19).

As used herein, the term "hyperinsulinemia" refers to the presence of an abnormally elevated level of insulin in the blood.

As used herein, the term "secretagogue" means a substance or compound that stimulates secretion. For example, an insulin secretagogue is a substance or compound that stimulates secretion of insulin.

As used herein, the term "hemoglobin" or "Hb" refers to a respiratory pigment present in erythrocytes, which is largely responsible for oxygen transport. A hemoglobin molecule comprises four polypeptide subunits (two a chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to $HbA_0$ for distinguishing it from glycated hemoglobin, which is referred to as "$HbA_1$," described infra) having $\alpha_2\beta_2$ subunits. Trace components such as $HbA_2(\alpha_2\delta_2)$ can also be found in normal adult hemolysate. Among classes of adult hemoglobin HbAs, there is a glycated hemoglobin (referred to as "$HbA_1$," or "glycosylated hemoglobin"), which may be further fractionated into $HbA_{1a1}$, $RbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement. The term "glycosylated hemoglobin" (also referred to as "$HbA_{1c}$,", "GHb", "hemoglobin-glycosylated", "diabetic control index" and "glycohemoglobin"; hereinafter referred to as "hemoglobin $A_{1c}$") refers to a stable product of the nonenzymatic glycosylation of the β-chain of hemoglobin by plasma glucose. Hemoglobin $A_{1c}$ comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S., et al., *Diabetes* (1989) 38: 1539-1543; Peters A., et al., *JAMA* (1996) 276: 1246-1252).

As used herein, the term "symptom of diabetes", includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood). The term "complication of diabetes" includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

As used herein, the term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels. The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue. Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL, VLDL and depressed levels of HDL). Exemplary Primary Hyperlipidemia include, but are not limited to, the following: (1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood; (2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma; (3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased; (4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels; (5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

As used herein, the terms "obese" and "obesity" refers to, according to the World Health Organization, a Body Mass Index (BMI) greater than 27.8 $kg/m^2$ for men and 27.3 $kg/m^2$ for women (BMI equals weight (kg)/height ($m^2$). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172-181; and Knowler, et al., *Am. J. Clin. Nutr.* (1991) 53:1543-1551).

One skilled in the art will recognize that, where not otherwise specified, the reaction step(s) is performed under suitable conditions, according to known methods, to provide the desired product.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention is directed to a process for the preparation of a compound of formula (I) and further to a process for the preparation of a compound of formula (II), as outlined in more detail in Scheme 1 below.

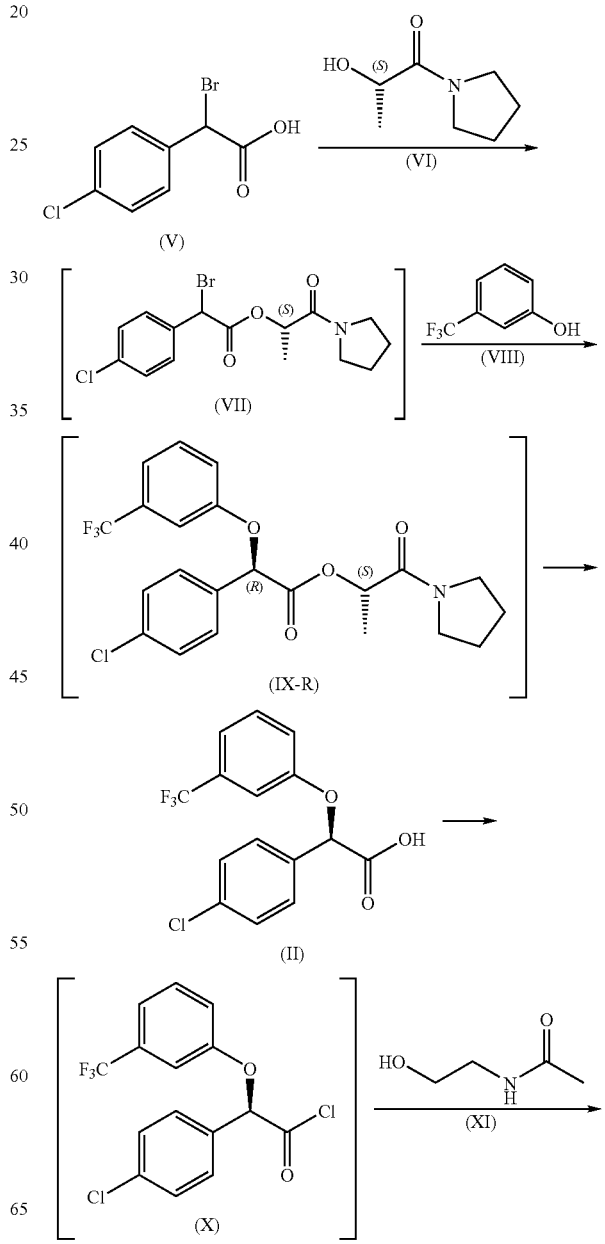

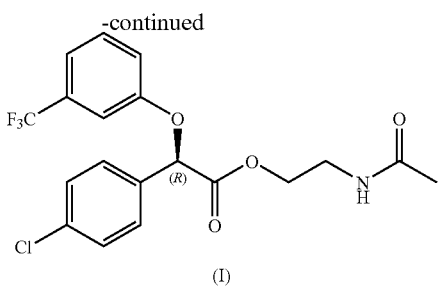

(I)

Accordingly, a compound of formula (V), also known as bromo-(4-chloro-phenyl)-acetic acid, is reacted with a compound of formula (VI), also known as 2(S)-hydroxy-1-pyrrolidin-1-yl-propan-1-one; wherein the compound of formula (VI) is preferably present in an amount in the range of from about 1.0 to about 1.5 molar equivalents (relative to the moles of the compound of formula (V)), more preferably in an amount in the range of from about 1.0 to about 1.1 molar equivalents, most preferably in an amount of about 1.02 molar equivalents;

in the presence of a first catalyst such as dimethylaminopyridine (DMAP), hydroxybenzotriazole (HOBt), and the like, preferably DMAP; wherein the first catalyst is preferably present in an amount in the range of from about 0.01 to abut 0.1 molar equivalents (relative to the moles of the compound of formula (V)), more preferably in a catalytic amount; in the presence of coupling agent such as dicyclohexylcarbodiimide (DCC), carbonyldiimidazole, (CDI), disuccinimidylcarbonate (DSC), bisnitrophenylcarbonate (BNPC), and the like, preferably DCC; wherein the coupling agent is preferably present in an amount in the range of from about 1.0 to about 1.2 molar equivalents (relative to the moles of the compound of formula (V)), more preferably in an amount in the range of from about 1.0 to about 1.1 molar equivalents, most preferably in an amount of about 1.02 molar equivalents;

in an aprotic organic solvent or mixture thereof, such as toluene, THF, MTBE, cyclohexane, 2-methyl-THF, ethyl acetate, and the like, preferably toluene; preferably at a temperature in the range of from about −10° C. to about 30° C.; to yield the corresponding compound of formula (VII), also known as bromo-(4-chloro-phenyl)-acetic acid-(1S)-methyl-2-oxo-2-pyrrolidin-1-yl-ethyl ester (50:50 mixture of diastereomers). Preferably, the compound of formula (VII) is not isolated.

The compound of formula (VII) is reacted with a compound of formula (VIII) also known as 3-trifluoromethyl-phenol, wherein the compound of formula (VIII) is present as its corresponding salt form, such as its corresponding LiOH salt, LiH salt, and the like, preferably LiOH*$H_2O$ salt; wherein the compound of formula (VIII) is preferably present in an amount in the range of from about 1.0 to about 3.0 molar equivalents (relative to the moles of the compound of formula (VII)), more preferably in an amount in the range of from about 1.0 to about 1.5 molar equivalents, most preferably in an amount of about 1.2 molar equivalents;

in the presence of a second catalyst such as NaI, and the like; wherein the second catalyst is preferably present in an amount in the range of from about 0.05 to about 1.0 molar equivalents (relative to the moles of the compound of formula (VII)), more preferably in a catalytic amount;

in an organic solvent or mixture thereof, such as THF, 2-Me-THF, toluene, and the like, preferably THF; preferably at a temperature in the range of from about −15° C. to about 10° C., preferably at about −5° C.; to yield the corresponding compound of formula (IX-R), also known as (4-chloro-phenyl)-2(R)-(3-trifluoromethyl-phenoxy)-acetic acid 1-(S)-methyl-2-oxo-2-pyrrolidin-1-yl-ethyl ester. Preferably, the compound of formula (IX-R) is not isolated.

Alternatively, the compound of formula (VIII), also known as 3-trifluoromethylphenol is reacted with a base such as LiOH, LiH, and the like (wherein the base is selected such that it is capable of capturing the HBr acid which is produced in the reaction of the compound of formula (VII) with the compound of formula (VIII) and/or further capable of deprotonating the compound of formula (VIII)); and then reacted with the compound of formula (VII), as described above; to yield the corresponding compound of formula The compound of formula (IX-R) is reacted with a suitably selected acid such as concentrated HCl, HBr, $H_2SO_4$, methanesulfonic acid, and the like, preferably concentrated HCl; preferably neat; preferably at a temperature greater than about room temperature, more preferably at a temperature in the range of from about 70° C. to about 150° C., more preferably at about 80° C.; to yield the corresponding compound of formula (II), also known as (−)-(4-chloro-phenyl)-(3-trifluoromethyl-phenoxy)-acetic acid (the corresponding (R)-enantiomer).

Preferably, the compound of formula (II) is prepared in an enantiomeric excess of about 85% or greater. More preferably, the compound of formula (II) is prepared in an enantiomeric excess of about 90% or greater. More preferably, the compound of formula (II) is prepared in an enantiomeric excess of about 95% or greater. More preferably, the compound of formula (II) is prepared in an enantiomeric excess of about 98% or greater. More preferably, the compound of formula (II) is prepared in an enantiomeric excess of about 99% or greater.

One skilled in the art will recognize that in the reaction of the compound of formula (IX-R) to yield the compound of formula (II) there is no significant amount of racemization, yielding a process which is advantageous for large scale manufacture of the compound of formula (I).

Preferably, the compound of formula (II) is further purified according to known methods. More preferably, the compound of formula (II) is crystallized from a suitably selected solvent or mixture thereof, such as a mixture of toluene and petrol ether (distillation fraction with a boiling range of 60° C. to 90° C.), a mixture of toluene and n-heptane, a mixture of toluene and n-hexane, a mixture of toluene and n-pentane, and the like, preferably from a mixture of toluene and petrol ether.

The compound of formula (II) is reacted with source of chlorine such as oxalyl chloride, $PCl_3$, thionyl chloride, and the like, preferably thionyl chloride; wherein the source of chlorine is preferably present in an amount in the range of from about 1.2 to about 2.5 molar equivalents (relative to the moles of the compound of formula (II)), more preferably in an amount in the range of from about 1.2 to about 1.6 molar equivalents, most preferably in an amount of about 1.4 molar equivalents;

neat or in an organic solvent such as toluene, xylene, DCE or other halogenated solvents; preferably at a temperature in the range of from about 50° C. to about 120° C., more preferably at a temperature in the range of from about 75° C. to about 100° C., most preferably at about 95° C.; to yield the corresponding compound of formula (X), also known as (−)-(4-chloro-phenyl)-(3-trifluoromethyl-phenoxy)-acetyl chloride (the corresponding (R) enantiomer). Preferably, the compound of formula (X) is not isolated.

The compound of formula (X) is reacted with a compound of formula (XI), also known as N-(2-hydroxy-ethyl)-acetamide; wherein the compound of formula (XI) is preferably present in an amount in the range of from about 1.0 to about 3.0 molar equivalents (relative to the moles of the compound of formula (X)), more preferably in an amount in the range of from about 1.2 to about 2.0 molar equivalents, most preferably in an amount of about 1.4 molar equivalents;

neat or in an organic solvent such as dimethylacetamide (DMA), acetone, acetonitrile, N-methylpyrrolidone, and the like, preferably dimethylacetamide; preferably at a temperature greater than about room temperature, more preferably at a temperature in the range of from about 0° C. to about 40° C., more preferably at a temperature in the range of from about 0° C. to about 20° C., more preferably at a temperature of about 20° C., to yield the corresponding compound of formula (I), also known as (−)-(4-chloro-phenyl)-(3-trifluoromethyl-phenoxy)-acetic acid 2-acetylamino-ethyl ester (the corresponding (R)-enantiomer).

Preferably, the solvent or mixture of solvents used in the reaction of the compound of formula (IX) with the source of chlorine is the same as the solvent or solvent mixture used in the reaction of the compound of formula (X) with the compound of formula (XI).

Preferably, the compound of formula (I) is isolated according to known methods, for example by filtration, solvent removal, and the like. Preferably, the compound of formula (I) is further purified, according to known methods, for example by column chromatography, recrystallization, and the like.

The present invention is further directed to a process for the recrystallization of the compound of formula (I). More particularly, the present invention is directed to a process for the recrystallization of the compound of formula (I)

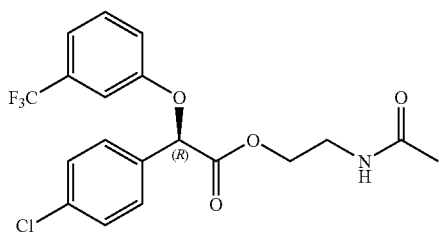 [SMILES: CC(=O)NCCOC(=O)[C@H](Oc1cccc(C(F)(F)F)c1)c1ccc(Cl)cc1]

(I)

comprising the following steps:

STEP A: adding the compound of formula (I) to a suitably selected solvent such as diisopropyl ether, and the like;

STEP B: heating the mixture of STEP A, preferably to about 55° C.; then optionally filtering the resulting mixture;

STEP C: cooling the mixture prepared in STEP B to a temperature in the range of from about −10° C. to about 0° C., preferably to about −5° C., for example in an ice/water bath; to yield a precipitate of the compound of formula (I);

STEP D: isolating the precipitate prepared in STEP C according to known methods, preferably by filtration and drying;

The recrystallization of the compound of formula (I) of the present invention utilizes a single solvent rather than a solvent and anti-solvent combination, thereby avoid potential formation of an intermediate oil. Thus the recrystallization of the present invention yields better manufacturing control and/or higher purity of the final crystallized product; and is thereof advantageous for large scale manufacture of the compound of formula (I).

The present invention further comprises pharmaceutical compositions containing a compound of formula (I) prepared according to the process as herein describes with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-1000 mg or any range therein, and may be given at a dosage of from about 0.01-500 mg/kg/day, or any range therein, preferably from about 0.1-250 mg/kg/day, or any range therein, preferably from about 0.5-100 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating metabolic disorders described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 100 to 1000 mg of the compound of formula (I) prepared according to the process as herein described, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The compound of formula (I), prepared according to the process as herein described may be administered in any of the foregoing compositions and according to dosage regimens established in the art whenever treatment of metabolic disorders is required.

The daily dosage of the products may be varied over a wide range from 0.01 to 3,500 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any range therein. Preferably, the range is from about 0.1 to about 250.0 mg/kg of body weight per day, or any range therein. More preferably, from about 0.5 to about 100.0 mg/kg of body weight per day, or any range therein. More preferably, from about 10.0 to about 100.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1 through 3 which follow herein describe recipes/procedures for the synthesis of the title compounds. Several batches of the said compounds were prepared according to the recipes/procedures as described below. Further, the physical properties listed at the end of the synthesis descriptions are physical properties measured for a representative samples of the prepared compound.

Example 1

Preparation of (−)-(4-Chloro-phenyl)-(3-trifluoromethyl-phenoxy)-acetic acid

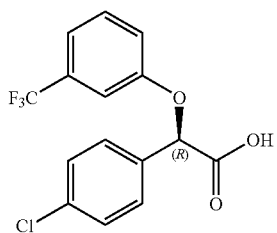

STEP A:

DCC (42.18 g, 0.204 mol) was dissolved in toluene (50 mL) and stirred at room temperature. α-Bromo-4-chlorophenylacetic acid (50.00 g, 0.200 mol) toluene (50 mL) and (S)—N,N-tetramethylene-lactamide (29.27 g, 0.204 mol) were placed into a 500 mL flask. The resulting yellow solution was then cooled to 0° C. To the solution was added DMAP (25.5 mg, 0.0002 mol) and then dropwise, at 0° C. the prepared DCC in toluene solution. The resulting suspension was stirred at 0° C. for 3 hours, then at room temperature for 6 hours. Dicyclohexylurea (prepared as a byproduct) was filtered off and washed with toluene (100 mL). The filtrate (containing the desired product, bromo-(4-chloro-phenyl)-acetic acid 1-(S)-methyl-2-oxo-2-pyrrolidin-1-yl-ethyl ester) was then transferred to a 1 L reactor for the next step.

STEP B: Preparation of Lithium-Phenolate Solution

LiOH.H$_2$O (9.35 g, 0.228 mol) was suspended in THF (100 mL). 3-(trifluoromethyl)phenol (39.0 g, 0.241 mol) was added and the resulting solution stirred at room temperature for 2 hours. The THF was evaporated and replaced with dry THF (100 mL).

STEP C: Nucleophilic Substitution

Sodium iodide (3.03 g, 0.02 mol) was added to the filtrate solution prepared as in Step A above. The resulting suspension was stirred at room temperature for 1 hour, then cooled to −15° C. To the resulting mixture was then added the lithium-phenolate solution prepared as in STEP B, at −15° C., over about 3 hours and the resulting solution stirred at −15° C. for 8 hours. The reaction was then quenched with phosphoric acid (7.5 g, 0.065 mol) at −13° C. and the cooling was switched off. Water (50 mL) was added and the aqueous phase separated. The organic phase was then washed with 5% NaHCO$_3$ solution (50 g), 36% Na$_2$S$_2$O$_3$ solution (50 g) with 60 minutes of stirring and water (50 g). To the washed organic phase was then added water (100 g) in two portions. THF and toluene were azeotropically removed at about 95-125° C. to yield (4-chloro-phenyl)-(R)-(3-trifluoromethyl-phenoxy)-acetic acid 1-(S)-methyl-2-oxo-2-pyrrolidin-1-yl-ethyl ester as a residue.

STEP D: Hydrolysis

To the residue prepared in STEP C above was added water (10 g) and a 36-38% HCl solution (60 g). The resulting biphasic mixture was stirred at 80° C. for between about 4 and about 8 hours (till completion of the hydrolysis as determined by HPLC) The resulting mixture was then cooled to 60° C. and toluene (125 mL) added. The aqueous phase was discarded and the organic phase washed with water (50 mL). Toluene (about 80 g) was removed by distillation to dry the organic phase. The resulting solution was then cooled to 70° C. and petrol ether 60/90 (250 mL) was added. The resulting solution was further cooled to 37° C. and seeded. The resulting mixture was stirred for 30 minutes at 37° C., the resulting suspension then cooled to 0° C. over about 2.5 hours. The precipitated crystals were filtered off and washed with a mixture of toluene (5 mL 0 and petrol ether 60/90 (9 mL) to yield wet product. The wet product was dried in a vacuum at 30° C. to yield the title compound as an off-white solid.

% ee 97.5-99.5; chemical purity 97.5-99.5%

Example 2

Preparation of (−)-(4-Chloro-phenyl)-(R)-(3-trifluoromethyl-phenoxy)-acetic acid 2-acetylamino-ethyl ester

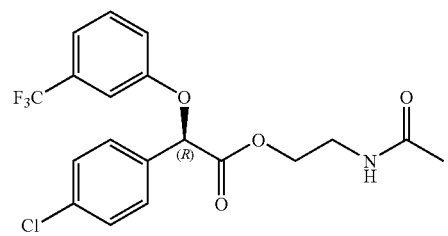 [SMILES: CC(=O)NCCOC(=O)[C@H](Oc1cccc(C(F)(F)F)c1)c1ccc(Cl)cc1]

(−)-(4-Chloro-phenyl)-(3-trifluoromethyl-phenoxy)-acetic acid (80.0 g, 242 mmol) was dissolved in toluene (485 mL) and the resulting mixture heated to 75° C. To the mixture was then added thionyl chloride (40.4 g, 340 mmol) over about 3 hours. The resulting solution was then heated to 95° C. for an additional 3 hours. The temperature of the resulting mixture was then adjusted to 70° C. and any excess thionyl chloride and some toluene removed by distillation. The resulting mixture was cooled to 0° C. and N-acethylethanolamine (38.7 g, 375 mmol) in DMA (32 mL) was added, at 0° C. over about 20 minutes. The resulting biphasic mixture was stirred at 0° C. for 60 minutes. The reaction was then quenched with water (80 mL) and an additional portion of toluene (210 mL) added. The resulting mixture was heated to 40° C., and the phases separated. The organic phase was washed 3 times with water (80 mL), the residual water removed by azeotropic distillation with toluene (about 130 g). To the resulting mixture was then added cylohexane (550 mL) at 40° C. and the mixture seeded. The resulting suspension was stirred at 40° C. for 2 hours, then cooled to 10° C. and stirred for an additional 2 hours. The precipitated crystals were filtered and washed with cold (10° C.) cyclohexane. The wet product was dried at 30° C. to yield the title compound as a white solid.

% ee 99.7-99.9; chemical purity 99.1-99.6%

Example 3

Recrystallization of (−)-(4-Chloro-phenyl)-(3-trifluoromethyl-phenoxy)-acetic acid 2-acetylamino-ethyl ester

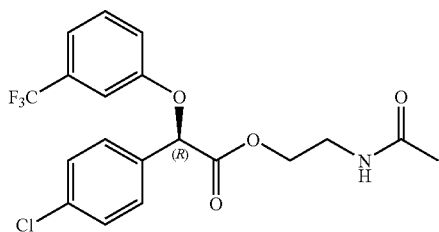

(−)-(4-Chloro-phenyl)-(R)-(3-trifluoromethyl-phenoxy)-acetic acid 2-acetylamino-ethyl ester (90.0 g) was dissolved in diisopropylether (900 mL) at 55° C. The resulting mixture was polish filtered, the solution cooled to 44° C. over about 20 minutes and seeded. The resulting mixture was stirred for 1 hour at 44° C., cooled to 35° C. over 4 hours, then stirred at 35° C. for 2 hours to yield a thick suspension. The suspension was cooled to −5° C. over about 5 hours and then stirred at −5° C. The resulting crystals were filtered off with a centrifuge and washed with precooled (−5° C.) diisopropylether (100 mL). The wet product was dried at 30° C. to yield the title compound as a white crystalline solid, more specifically as white crystals, needles.

Example 4

Oral Formulation—Prophetic Example

As a specific embodiment of an oral composition, 100 mg of the compound prepared as in Example 3 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A process for preparing the compound of formula (I):

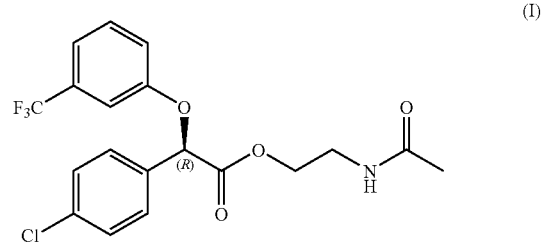 [SMILES: CC(=O)NCCOC(=O)[C@H](Oc1cccc(C(F)(F)F)c1)c1ccc(Cl)cc1]

comprising:
(a) reacting the compound of formula (IX-R):

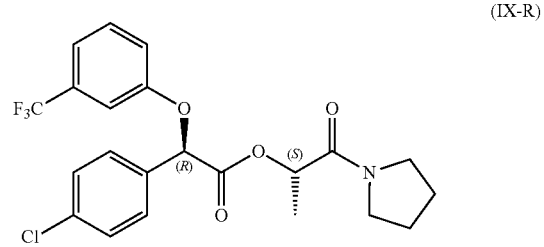

with an acid at a temperature of from about 70° C. to about 150° C. to yield the compound of formula (II):

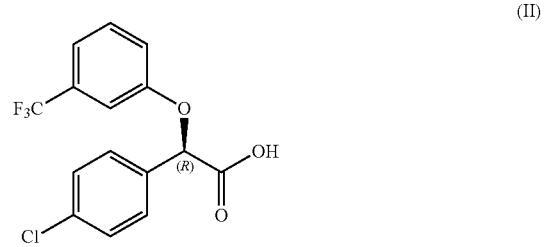

having an enantiomeric excess of about 99% or greater;
(b) reacting the compound of formula (II) with a source of chlorine, neat or in an organic solvent, to yield the compound of formula (X):

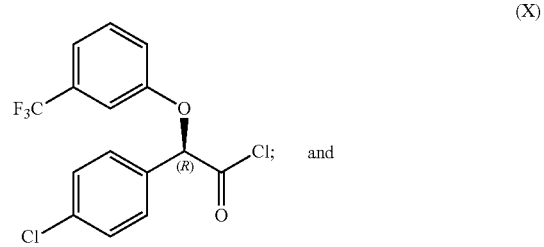

and (c) reacting the compound of formula (X) with a compound of formula (XI):

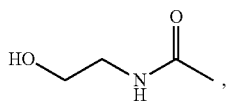

(XI)

neat or in an organic solvent, to yield the compound of formula (I).

2. The process of claim 1 further comprising preparing the compound of formula (IX-R) by reacting the compound of formula (VII):

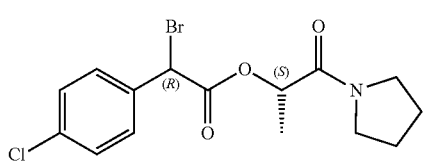

(VII)

with a salt of the compound of formula (VIII):

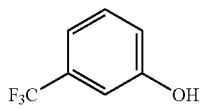

(VIII)

in the presence of a second catalyst, in an organic solvent or mixture thereof to yield the compound of formula (IX-R).

3. The process of claim 2 further comprising preparing the compound of formula (VII) by reacting the compound of formula (V):

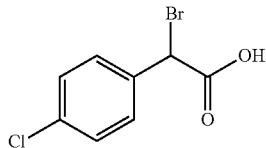

(V)

with a compound of formula (VI):

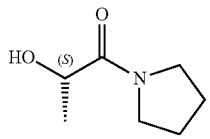

(VI)

in the presence of a first catalyst and a coupling agent, in an aprotic organic solvent or mixture thereof, to yield the compound of formula (VII).

4. The process of claim 1 where the source of chlorine is thionyl chloride.

5. The process of claim 4 where the thionyl chloride is present in an amount in the range of from about 1.2 to about 2.5 molar equivalents with respect to the compound of formula (II).

6. The process of claim 5 where the thionyl chloride is present in an amount of about 1.4 molar equivalents with respect to the compound of formula (II).

7. The process of claim 1 where the compound of formula (XI) is present in an amount in the range of from about 1.0 to about 3.0 molar equivalents with respect to the compound of formula (X).

8. The process of claim 7 where the compound of formula (XI) is present in an amount of about 1.4 molar equivalents with respect to the compound of formula (X).

9. The process of claim 1 where step (b) is carried out in dimethylacetamide.

10. The process of claim 1 where step (b) is carried out at a temperature of about 80° C.

11. The process of claim 1 where step (c) is carried out in dimethylacetamide.

12. The process of claim 1 where step (c) is carried out at a temperature of about 20° C.

13. The process of claim 1 where the acid of step (a) is selected from the group consisting of concentrated HCl, HBr, $H_2SO_4$ and methanesulfonic acid.

14. The process of claim 13 where the acid is concentrated HCl.

15. The process of claim 1 where the compound of formula (IX-R) is reacted with the acid neat.

16. The process of claim 1 where the compound of formula (IX-R) is reacted with the acid at a temperature of about 80° C.

17. The process of claim 1, further comprising crystallizing the compound of formula (II) from a mixture of toluene and petrol ether.

18. The process of claim 2 where the salt of the compound of formula (VIII) is the salt formed with $LiOH*H_2O$.

19. The process of claim 18 where the salt of the compound of formula (VIII) is present in an amount in the range of from about 1.0 to about 3.0 molar equivalents with respect to the compound of formula (VII).

20. The process of claim 19 where the salt of the compound of formula (VIII) is present in about 1.2 molar equivalents with respect to the compound of formula (VII).

21. The process of claim 2 where the second catalyst is NaI.

22. The process of claim 2 where the compound of formula (VII) is reacted with the salt of the compound of formula (VIII) in THF.

23. The process of claim 2 where the compound of formula (VII) is reacted with the salt of the compound of formula (VIII) at about −5° C.

24. The process of claim 3 where the compound of formula (VI) is present in an amount in the range of from about 1.0 to about 1.5 molar equivalents with respect to the compound of formula (V).

25. The process of claim 3 where the first catalyst is dimethylaminopyridine and the coupling agent is dicyclohexylcarbodiimide.

26. The process of claim 3 where the aprotic solvent is toluene.

27. The process of claim 3 where the compound of formula (V) is reacted with the compound of formula (VI) at a temperature in the range of from about −10° C. to about 30° C.

* * * * *